(12) United States Patent
Yang et al.

(10) Patent No.: US 12,076,684 B2
(45) Date of Patent: Sep. 3, 2024

(54) METHOD AND SYSTEM FOR AUTOMATICALLY CLEANING AIR FILTERS OF A MEDICAL IMAGING SYSTEM

(71) Applicant: GE Precision Healthcare LLC, Wauwatosa, WI (US)

(72) Inventors: Yalan Yang, Wuxi (CN); Kai Ji, Wuxi (CN); Fenggui Huang, Wuxi (CN); Jie Wang, Wuxi (CN); Ying Zhang, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 208 days.

(21) Appl. No.: 17/532,845

(22) Filed: Nov. 22, 2021

(65) Prior Publication Data

US 2023/0158438 A1     May 25, 2023

(51) Int. Cl.
*B01D 46/681* (2022.01)
*A61B 8/00* (2006.01)
(Continued)

(52) U.S. Cl.
CPC .......... *B01D 46/681* (2022.01); *A61B 8/546* (2013.01); *A61B 8/56* (2013.01); *B01D 33/46* (2013.01);
(Continued)

(58) Field of Classification Search
None
See application file for complete search history.

(56) References Cited

U.S. PATENT DOCUMENTS 6,632,269 B1 * 10/2003 Najm ................. B01D 46/20
 55/501
9,183,723 B2   11/2015 Sherman et al.
(Continued)

FOREIGN PATENT DOCUMENTS

CN       102824795 A    12/2012
CN       111185050 A     5/2020
(Continued)

OTHER PUBLICATIONS

JPH08152242A_ENG (Espacenet machine translation of Kobayashi) (Year: 1996).*
KR20170090254A_ENG (Espacenet machine translation of Hong) (Year: 2017).*

*Primary Examiner* — Gabriel E Gitman
(74) *Attorney, Agent, or Firm* — McAndrews, Held & Malloy, Ltd.; Daniel Bissing; David Bates

(57) ABSTRACT

A system and method for automatically cleaning air filters of a medical imaging system is provided. The method includes monitoring an air filter operating condition, determining that the air filter operating condition is not within a pre-determined threshold, and providing a control signal to at least one air filter. The at least one air filter comprises a motor, drive shaft, rotatable passive shaft, continuous belt air filter, and a stationary filter brush. The drive shaft is rotatably coupled to the motor. The continuous belt air filter is coupled to the drive shaft and the passive shaft. The stationary filter brush is mounted against the continuous belt air filter. The method includes rotating, by the motor in response to the control signal, the drive shaft to translate the continuous belt air filter around and between the drive shaft and the rotatable passive shaft, and across the stationary filter brush.

23 Claims, 6 Drawing Sheets

(51) Int. Cl.
*B01D 33/46* (2006.01)
*B01D 46/00* (2022.01)
*B01D 46/18* (2006.01)
*B01D 46/42* (2006.01)
*B01D 46/44* (2006.01)
*B01D 46/46* (2006.01)
*B01D 46/52* (2006.01)
*B01D 46/69* (2022.01)
*B08B 17/02* (2006.01)
*H05K 7/20* (2006.01)

(52) U.S. Cl.
CPC ......... *B01D 46/0049* (2013.01); *B01D 46/18* (2013.01); *B01D 46/4227* (2013.01); *B01D 46/444* (2013.01); *B01D 46/446* (2013.01); *B01D 46/46* (2013.01); *B01D 46/528* (2013.01); *B01D 46/69* (2022.01); *B08B 17/02* (2013.01); *H05K 7/20181* (2013.01); *B01D 2273/30* (2013.01); *B01D 2279/45* (2013.01)

(56) References Cited

U.S. PATENT DOCUMENTS

| | | | | |
|---|---|---|---|---|
| 2006/0070527 | A1* | 4/2006 | Chapman | B01D 46/46 96/417 |
| 2006/0109956 | A1* | 5/2006 | Lacey | A61B 6/035 378/199 |
| 2007/0239001 | A1* | 10/2007 | Mehi | G01S 7/52095 600/437 |
| 2008/0239245 | A1* | 10/2008 | Kitahara | H05K 7/20145 353/61 |
| 2011/0297000 | A1 | 12/2011 | Kotani et al. | |
| 2015/0351288 | A1* | 12/2015 | Fukuda | H05K 7/20181 361/679.48 |
| 2021/0205742 | A1* | 7/2021 | Chamarthi | B01D 33/46 |

FOREIGN PATENT DOCUMENTS

JP      H08152242 A   *   6/1996  ............. B01D 46/20
KR    20170090254 A   *   8/2017

* cited by examiner

METHOD AND SYSTEM FOR AUTOMATICALLY CLEANING AIR FILTERS OF A MEDICAL IMAGING SYSTEM

FIELD

Certain embodiments relate to medical imaging system air filters, and particularly automatic cleaning ultrasound system air filters. More specifically, certain embodiments relate to a method and system for automatically cleaning air filters of a medical imaging system, such as an ultrasound system.

BACKGROUND

Medical imaging systems, such as ultrasound systems, may include cooling mechanisms for preventing overheating of electronics housed within the medical imaging system. The cooling systems may include an air filter for filtering ambient temperature air drawn into the medical imaging system. The filtered ambient temperature air may be passed over the electronics to transfer heat from the electronics to the air. The heated air may then be expelled from the medical imaging system. Conventional air filters of medical imaging system cooling systems require periodic replacement and/or cleaning. The replacement or cleaning of the air filter is typically performed manually, which may be inconvenient and inefficient. Failure to timely clean or replace a dusty air filter may cause overheating of the electronics, which may degrade system performance or even result in system failure.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for automatically cleaning air filters of a medical imaging system, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
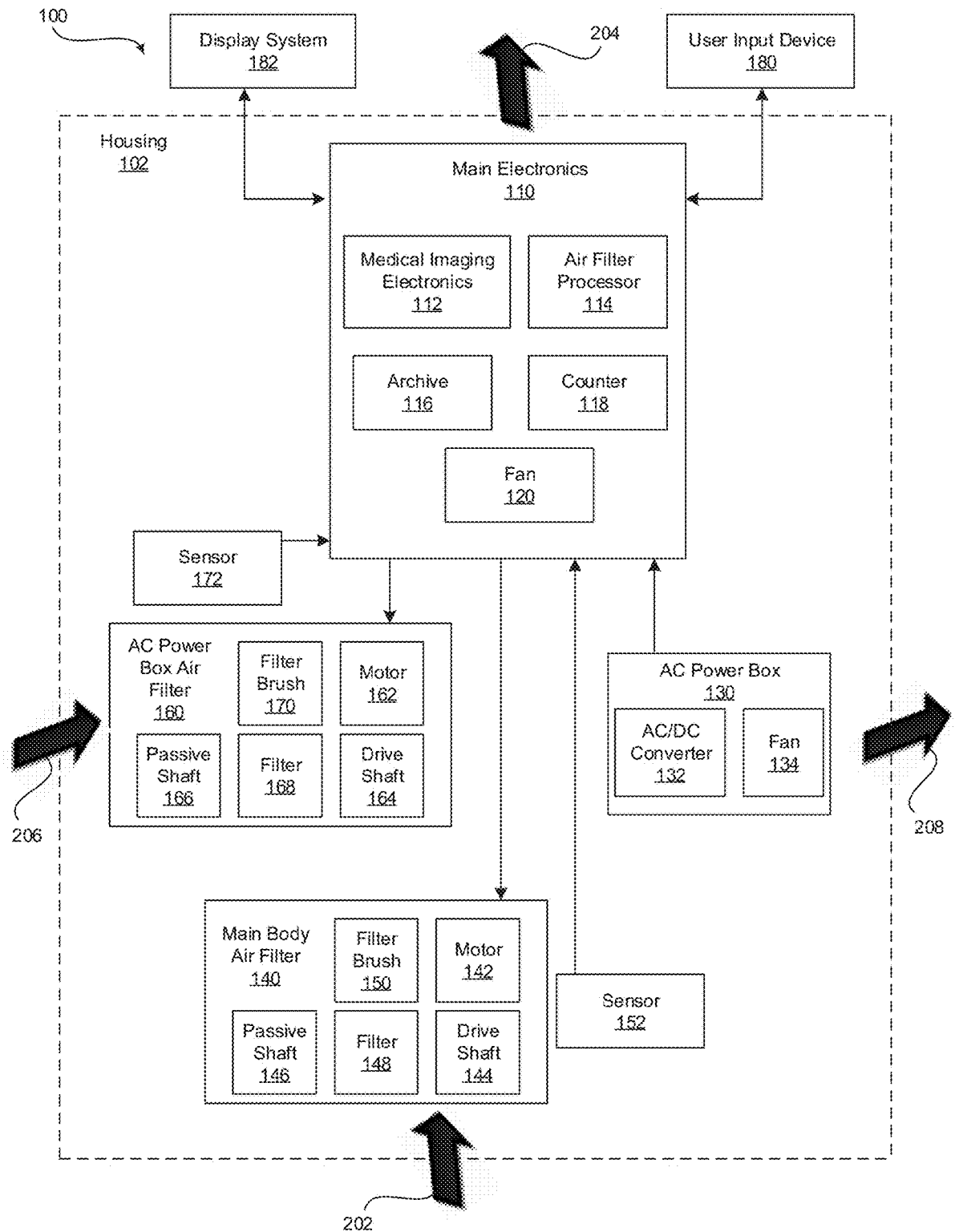
FIG. 1 is a block diagram of an exemplary medical imaging system having air filters that are operable to be automatically cleaned, in accordance with various embodiments.

Certain embodiments may be found in a method and system for automatically cleaning air filters of a medical imaging system. Aspects of the present disclosure have the technical effect of automatically providing a control signal to activate a motor that drives a drive shaft to automatically clean an air filter of a medical imaging system in response a tracked amount of time the medical imaging system is powered on exceeding a pre-determined threshold. Various embodiments have the technical effect of automatically providing a control signal to activate a motor that drives a drive shaft to automatically clean an air filter of a medical imaging system in response to a monitored air flow characteristic falling outside of a pre-determined threshold. Certain embodiments have the technical effect of automatically cleaning an air filter of a medical imaging system without user intervention (e.g., manual cleaning or replacement of the air filter).

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

Figure 2:
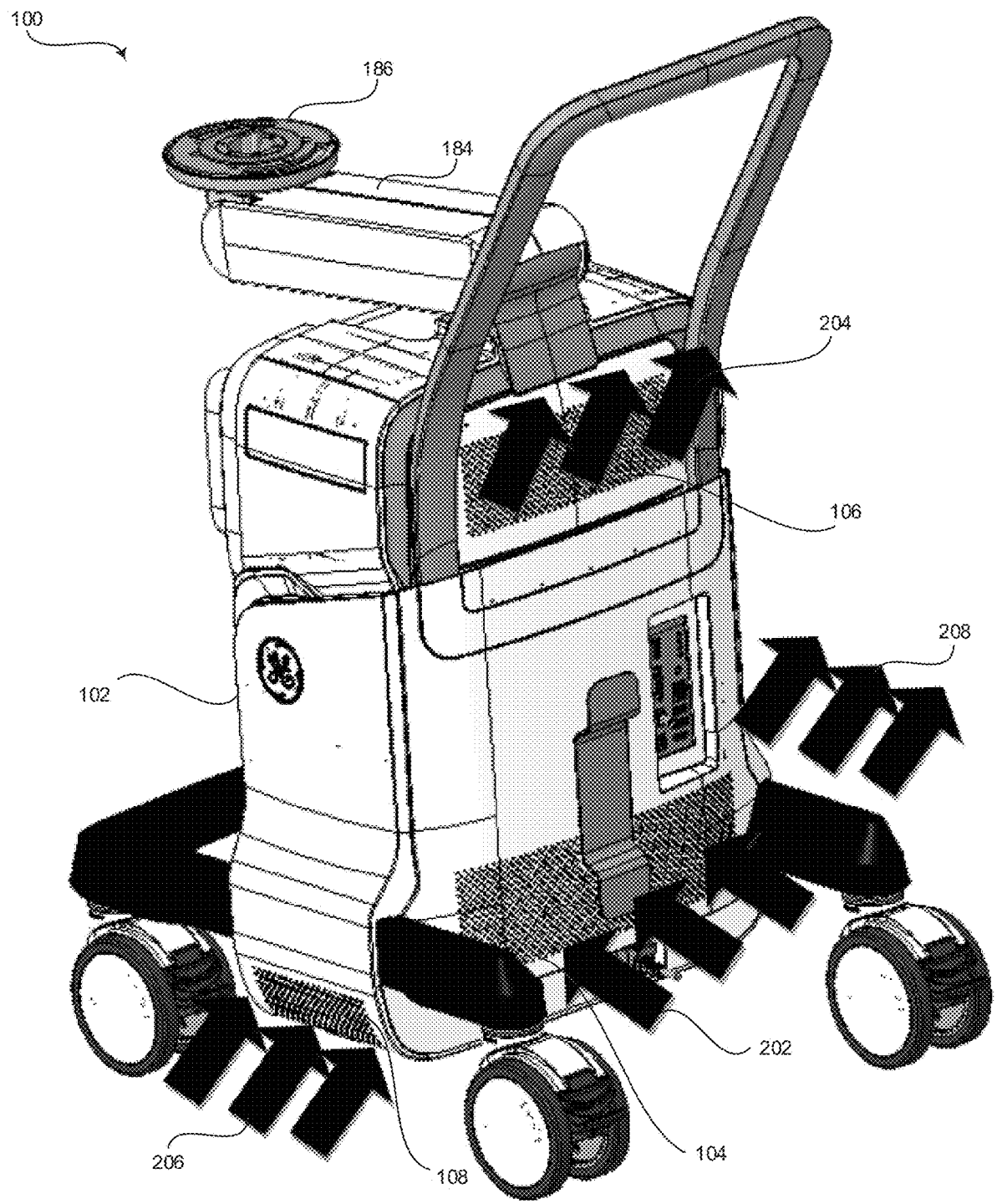
FIG. 2 is a perspective view of an exemplary ultrasound system having air inlets for receiving ambient temperature air and air outlets for expelling warmed air, in accordance with various embodiments.
Figure 3:
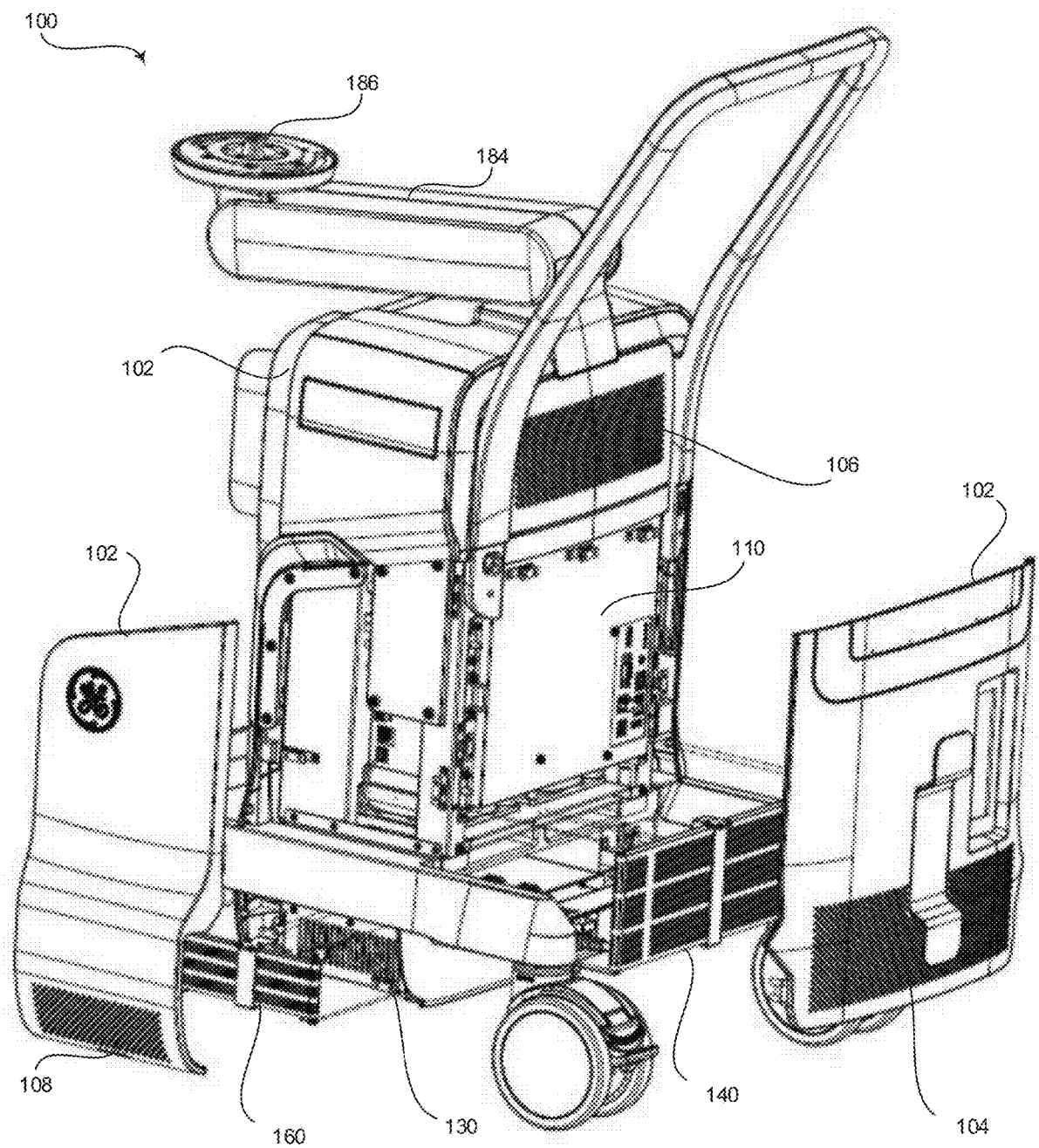
FIG. 3 is an exploded view of the exemplary ultrasound system of FIG. 2, illustrating exemplary automatic cleaning air filter assemblies, in accordance with various embodiments.

It should be noted that various embodiments are described herein with reference to an ultrasound system. For example, FIGS. 2 and 3 illustrate an exemplary ultrasound system. However, aspects of the present invention are not limited to ultrasound systems. Instead, any medical imaging system utilizing an air filter is contemplated.

FIG. 1 is a block diagram of an exemplary medical imaging system 100 having air filters 140, 160 that are operable to be automatically cleaned, in accordance with various embodiments. Referring to FIG. 1, there is shown a medical imaging system 100. The medical imaging system 100 comprises main electronics 110, an AC power box 130, a main body air filter 140, an AC power box air filter 160, and air flow characteristic sensors 152, 172 disposed in a housing 102. The medical imaging system 100 further comprises a user input device 180 and a display system 182 communicatively coupled to the main electronics 110.

The user input device 180 may be utilized to input patient data, medical imaging parameters, settings, select protocols and/or templates, and the like. In an exemplary embodiment, the user input device 180 may be operable to configure, manage and/or control operation of one or more components and/or modules in the medical imaging system 100. In this regard, the user input device 180 may be operable to configure, manage and/or control operation of the medical imaging electronics 112, the air filter processor 114, the archive 116, the user input device 180, and/or the display system 182. The user input device 180 may include a touch panel, button(s), rotary encoder(s), motion tracking, voice recognition, a mousing device, keyboard, camera and/or any other device capable of receiving a user directive. In certain embodiments, one or more of the user input devices 180 may be integrated into other components, such as the display system 182, for example. As an example, user input device 180 may include a touchscreen display.

The display system 182 may be any device capable of communicating visual information to a user. For example, a display system 182 may include a liquid crystal display, a light emitting diode display, and/or any suitable display or displays. The display system 182 can be operable to present information from the medical imaging electronics 112, air filter processor 114, and/or archive 116, such as air filter cleaning settings, medical image data, and/or any suitable information.

The main electronics 110 comprises medical imaging electronics 112, an air filter processor 114, an archive 116, a counter 118, and a fan 120. The fan 120 may be configured to prevent the main electronics 110 from overheating by drawing ambient temperature air 202 into the housing 102, through the main body air filter 140, and across the main electronics 110. The heat produced by the main electronics 110 is transferred to the ambient temperature 202 air drawn into the medical imaging system housing 102. The warmed air 204 is then expelled from the housing 102.

The medical imaging electronics 112 may be configured to control acquisition of medical image data by a probe, scanner, or the like (not shown), receive the medical image data from the probe, scanner, or the like (not shown), and perform one or more processing operations according to a modality corresponding with the received medical image data. The medical imaging electronics 112 may comprise suitable logic, circuitry, interfaces and/or code that may be operable to process medical image data for generating medical images for presentation on the display system 182. In an exemplary embodiment, the medical imaging electronics 112 may be operable to perform display processing and/or control processing, among other things. Acquired medical image data may be processed in real-time during a medical imaging examination as the medical image data is received. Additionally or alternatively, the medical image data may be stored temporarily during a medical imaging examination and processed in less than real-time in a live or off-line operation. In various embodiments, the processed medical image data can be presented at the display system 182 and/or may be stored at the archive 116. The archive 116 may be a local archive, a Picture Archiving and Communication System (PACS), or any suitable device for storing medical images and related information. The medical imaging electronics 112 may comprise one or more central processing units, microprocessors, microcontrollers, and/or the like. The medical imaging electronics 112 may be an integrated component, or may be distributed across various locations, for example. In an exemplary embodiment, the medical imaging electronics 112 may be capable of receiving input information from user input devices 180 and/or archive 116, generating an output displayable by a display system 182, and manipulating the output in response to input information from a user input device 180, among other things.

The air filter processor 114 may comprise suitable logic, circuitry, interfaces and/or code that may be operable to provide a control signal to the main body air filter 140 and/or the AC power box air filter 160 to initiate automatic cleaning of the air filter(s) 140, 160. The air filter processor 114 may be configured to provide the control signal when it determines that a monitored air filter operating condition is no longer within a pre-determined threshold. The monitored air filter operating condition may include an amount of time the medical imaging system 100 has been powered on. Additionally and/or alternatively, the monitored air filter operating condition may include an air flow characteristic detected by a sensor 152, 172. The air flow characteristic may include a flow rate of the air measured by a mass flow rate sensor 152, 172, a pressure drop across an air filter 140, 160 measured by a differential pressure sensor 152, 172, or any suitable air flow characteristic measured by any suitable sensor, meter, valve, or the like. The air filter processor 114 may be configured to generate a control signal to send to an appropriate air filter 140, 160 in response to the determination that at least one monitored air filter operating condition is not within the pre-determined threshold. The control signal provided by the air filter processor 114 may activate a motor 142, 162 of the air filter 140, 160 to initiate automatic cleaning as described below in connection with the air filters 140, 160.

The air filter processor 114 may be one or more central processing units, microprocessors, microcontrollers, and/or the like. The air filter processor 114 may be an integrated component, or may be distributed across various locations, for example. In an exemplary embodiment, the air filter processor 114 may be capable of receiving input information from user input devices 180 and/or archive 116, monitor air filter operating conditions, and providing control signals to the air filters 140, 160 for initiating automatic cleaning of the air filters 140, 160, among other things. The air filter processor 114 may be capable of executing any of the method(s) and/or set(s) of instructions discussed herein in accordance with the various embodiments, for example.

The air filter processor 114 may comprise suitable logic, circuitry, interfaces and/or code that may be operable to monitor an amount of time the medical imaging system 100 has been powered on as tracked by a counter 118 to determine when to provide a control signal to the main body air filter 140 and/or the AC power box air filter 160 to initiate automatic cleaning of the air filter(s) 140, 160. For example, the main electronics 110 may comprise a counter 118 comprising suitable logic, circuitry, interfaces and/or code that may be operable to track an amount of time the medical imaging system 100 is powered on. The counter 118 may be configured to continuously increment when the medical imaging system 100 is powered on until the medical imaging system 100 is powered off. The counter 118 may be configured to resume incrementing when the medical imaging system 100 is powered on again. In various embodiments, the air filter processor 114 may continuously or periodically monitor the counter 118 to determine when a current powered on time of the medical imaging system 100 exceeds a pre-determined threshold. The pre-determined threshold may be set by a manufacturer, vendor, user, or the like. For example, the pre-determined threshold may be 7 days, 30 days, 60 days, or any suitable amount of time. In various embodiments, the pre-determined threshold may be the same or different for each air filter 140, 160 in the medical imaging system 100. The air filter processor 114 may be configured to provide a control signal to the appropriate air filter 140, 160 based on the pre-determined threshold associated with the respective air filter 140, 160. The air filter processor 114 may be configured to reset the counter 118 when the pre-determined threshold has been exceeded and the control signal sent to the air filter 140, 160.

The air filter processor 114 may comprise suitable logic, circuitry, interfaces and/or code that may be operable to monitor air flow characteristics provided by sensors 152, 172 to determine when to provide a control signal to the main body air filter 140 and/or the AC power box air filter 160 to initiate automatic cleaning of the air filter(s) 140, 160. The air flow characteristics may include mass flow rate through the air filter 140, 160, a pressure drop across the air filter 140, 160, or any suitable air flow characteristic. The air flow characteristic may be detected by a sensor 152, 172 and transmitted to the air filter processor 114 for processing. The sensor 152, 172 may be a mass flow rate sensor, a differential pressure sensor, or any suitable sensor. In various embodiments, the air filter processor 114 may continuously or periodically monitor the air flow characteristics provided by sensors 152, 172 to determine when the air flow characteristic of one of more of the air filters 140, 160 of the medical imaging system 100 is outside of a pre-determined threshold. The pre-determined threshold may be set by a manufacturer, vendor, user, or the like. For example, the pre-determined threshold may be a minimum mass flow rate, a maximum pressure drop, or any suitable value of an air flow characteristic. In various embodiments, the pre-determined threshold may be the same or different for each air filter 140, 160 in the medical imaging system 100. The air filter processor 114 may be configured to provide a control signal to the appropriate air filter 140, 160 based on the air flow characteristic of that air filter 140, 160 falling outside of the pre-determined threshold associated with the respective air filter 140, 160.

The archive 116 may be one or more computer-readable memories integrated with the medical imaging system 100 and/or communicatively coupled (e.g., over a network) to the medical imaging system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 116 may include databases, libraries, sets of information, or other storage accessed by and/or incorporated with the medical imaging electronics 112 and/or the air filter processor 114, for example. The archive 116 may be able to store data temporarily or permanently, for example. The archive 116 may be capable of storing medical image data, data generated by the medical imaging electronics 112 and/or air filter processor 114, and/or instructions readable by the medical imaging electronics 112 and/or air filter processor 114, among other things. In various embodiments, the archive 116 stores instructions for execution by the air filter processor 114 for monitoring the counter 118 and/or sensors 152, 172 to generate control signals for automatically cleaning the air filters 140, 160, for example.

The AC power box 130 may comprise an AC/DC converter 132 and a fan 134. The fan 134 may be configured to prevent the AC power box 130 from overheating by drawing ambient temperature air 206 into the housing 102, through the AC power box air filter 160, and across the AC power box 130. The heat produced by the AC power box 130 is transferred to the ambient temperature 206 air drawn into the medical imaging system housing 102. The warmed air 208 is then expelled from the housing 102. The AC/DC converter 132 may comprise suitable logic, circuitry, interfaces and/or code that may be operable to convert alternating current (AC) from an external power supply (not shown) to direct current (DC) for powering the components of the medical imaging system 100, such as the main electronics 110, fans 120, 134, sensor(s) 152, 172, air filters 140, 160, user input device 180, and/or display system 182.

The medical imaging system 100 may comprise one or more air filters 140, 160 configured to filter air 202, 206 drawn into the housing 102 of the medical imaging system 100 for cooling components of the medical imaging system 100, such as the main electronics 110 and the AC power box 130. For example, the one or more air filters 140 may comprise a main body air filter 140 for filtering air 202 passed over main electronics 110, an AC power box air filter 160 for filtering air 206 passed over the AC power box 130, and/or any suitable number of air filters 140, 160. The air filters 140, 160 may be manufactured in various sizes, such as a larger air filter 140, a smaller air filter 160, or any suitable number of sizes. The air filters 140, 160 may each comprise a motor 142, 162, a drive shaft 144, 164, a passive shaft 146, 166, a filter 148, 168, and a filter brush 150, 170. In various embodiments, one or more sensors 152, 172 may be positioned near each of the air filters 140, 160 for monitoring at least one air flow characteristic of the respective air filter 140, 160. The air filters 140, 160 may be configured to automatically clean the filter 148, 168 in response to receiving a control signal from the air filter processor 114. For example, the control signal may activate the motor 142 coupled to a drive shaft 144. The activated motor 142 may be configured to rotate the drive shaft 144 coupled to the filter 148. The filter 148 may be a continuous belt air filter extending around and between the drive shaft 144 and a rotatable passive shaft 146. As the motor 142 rotates the drive shaft 144, the filter 148 may translate around and between the drive shaft 144 and the passive shaft 146, and across a stationary filter brush 150 mounted between the drive shaft 144 and the passive shaft 146 against the filter 148. The translation of the filter 148 across the stationary filter brush 150 causes dust and other particles to be detached from the filter 148 to automatically clean the filter 148 of the air filter assembly 140, 160. The control signal provided by the air filter processor 114 may be provided to the motor 142 for a pre-determined amount of time sufficient to clean the filter 148 before shutting the motor off.

Components of the medical imaging system 100 may be implemented in software, hardware, firmware, and/or the like. The various components of the medical imaging system 100 may be communicatively linked. Components of the medical imaging system 100 may be implemented separately and/or integrated in various forms.

FIG. 2 is a perspective view of an exemplary ultrasound system 100 having air inlets 104, 108 for receiving ambient temperature air 202, 206 and air outlets 106 for expelling warmed air 204, 208, in accordance with various embodiments. FIG. 3 is an exploded view of the exemplary ultrasound system 100 of FIG. 2, illustrating exemplary automatic cleaning air filter assemblies 140, 160, in accordance with various embodiments. The ultrasound system 100 of FIGS. 2 and 3 may share various characteristics with the medical imaging system 100 of FIG. 1. Referring to FIGS. 2 and 3, the ultrasound system 100 may comprise a housing 102, an arm 184, a mount 186, main electronics 110, an AC power box 130, a main body air filter 140, and an AC power box air filter 160. The mount 186 may be configured to receive a user input device 180 and/or display system 182. The mount 186 may be coupled to an arm 184 extending from and coupled to the housing 102. The main electronics 110, AC power box 130, main body air filter 140, and AC power box air filter 160 may be disposed within the housing 102. The housing 102 may include air inlets 104, 108 through which ambient temperature air 202, 206 is drawn into the housing, through the air filters 140, 160 positioned adjacent the air inlets 104, 108, and across the main body electronics 110 or AC power box 130. The warmed air 204, 208 is expelled through air outlets 106 in the housing 102. For example, ambient temperature air 202 may be drawn through air inlet 104, passed through main body air filter 140, and passed across main electronics 110. The heat from the main electronics 110 may be transferred to the filtered air, and the warmed air 208 may be expelled through air outlet 106 in the housing 102. The main body air filter 140 may be mounted between the air inlet 104 and the main electronics 110. As another example, ambient temperature air 206 may be drawn through air inlet 108, passed through AC power box air filter 160, and passed across AC power box 130. The heat from the AC power box 130 may be transferred to the filtered air, and the warmed air 208 may be expelled through air outlet (not shown) in the housing 102. The AC power box air filter 160 may be mounted between the air inlet 108 and the AC power box 130.

Figure 4:
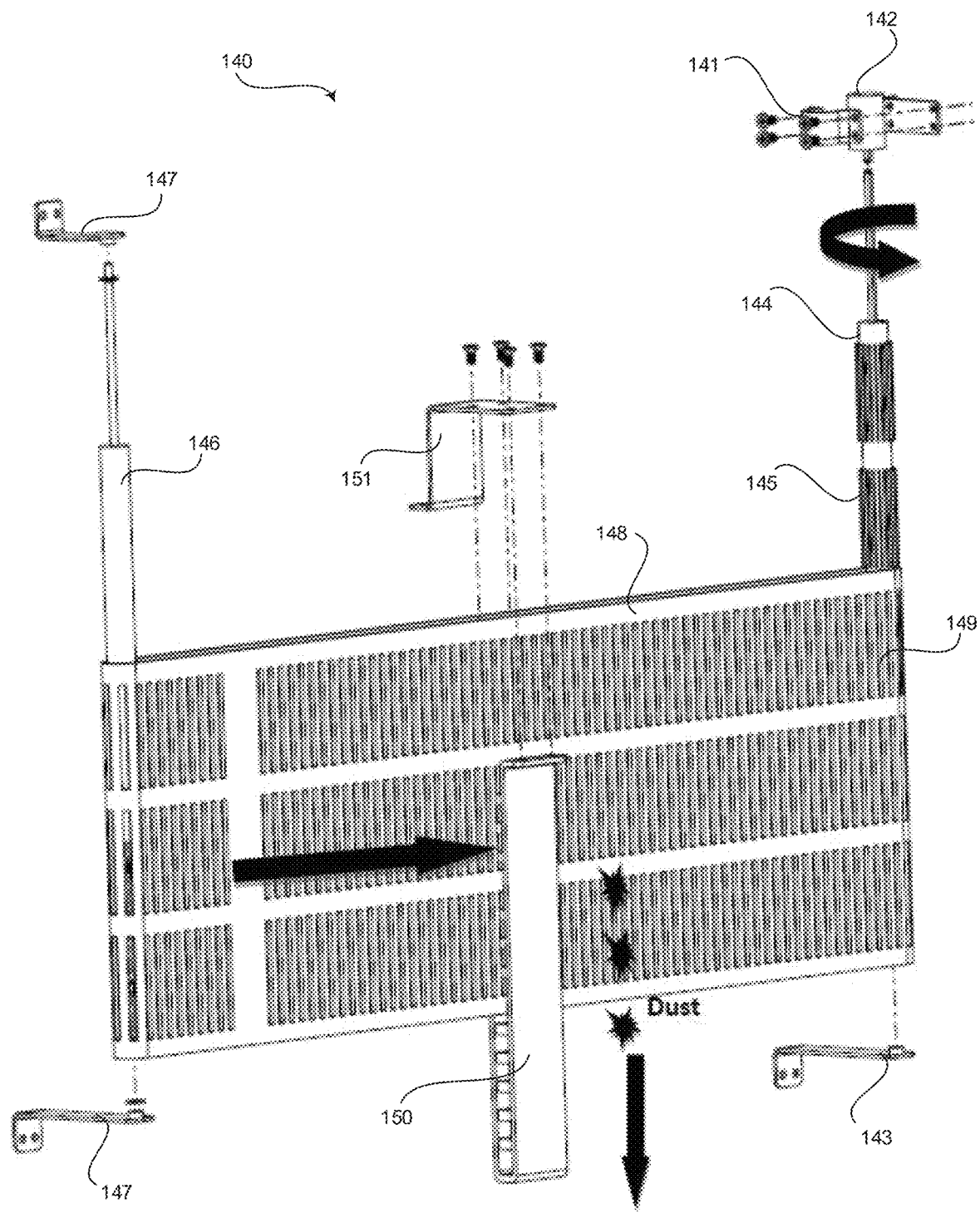
FIG. 4 is a perspective view of an exemplary automatic cleaning main body air filter assembly, in accordance with various embodiments.

FIG. 4 is a perspective view of an exemplary automatic cleaning main body air filter assembly 140, in accordance with various embodiments. Although the main body air filter 140 is shown in FIG. 4, the AC power box air filter 160 shares various characteristics with the main body air filter 140. For example, the AC power box air filter 160 may be smaller than the main body air filter 140 but may otherwise include the same components. Referring to FIG. 4, the main body air filter 140 comprises a motor 142, drive shaft 144, passive shaft 146, filter 148, and filter brush 150. The motor 142 may be mounted within a housing 102 of a medical imaging system 100 by mounting bracket 141. The motor 142 may receive a first end of the drive shaft 144. The second, opposite end of the drive shaft 144 may be rotatably mounted to mounting bracket 143. The motor 142 is configured to rotate the drive shaft 144 when activated. The drive shaft 144 may include grips 145 configured to engage with slots 149 of the filter 148. The grips 145 may be protrusions extending from drive shaft 144 that fit into the slots 149 of the filter 148. The filter 148 may be a continuous belt air filter that wraps around the drive shaft 148 on a first side and around a passive shaft 146 at a second side. The ends of the passive shaft 146 may be rotatably mounted within the housing 102 of the medical imaging system 100 by mounting brackets 147. The passive shaft 146 may optionally include grips (not shown) as provided on the drive shaft 144. The filter 148 may be configured to translate around and between the drive shaft 144 and the passive shaft 146 when the motor 142 is activated, thereby rotating the drive shaft 144. The filter brush 150 may be fixedly mounted within the housing 102 of the medical imaging system 100 by mounting bracket 151. The filter brush 150 may be held stationary against one or both outer sides of the filter 148 between the drive shaft 144 and the passive shaft 146.

In operation, the motor 142 is activated in response to receiving a control signal from the air filter processor 114. The motor 142 rotates the drive shaft 144 around the longitudinal (i.e., vertical) axis of the drive shaft 144. The grips 145 of the drive shaft 144 engage the slots 149 in the filter 148 to translate the continuous belt air filter 148 around the drive shaft 144 and the rotatable passive shaft 146. The translation of the filter 148 causes the filter 148 to move across the stationary filter brush 150 pressed against the outer sides of the filter 148 and/or extending into the slots 149 of the filter 148, which causes the filter brush 150 to dislodge dust and other particles clinging to the filter 148, thereby cleaning the filter 148 without user intervention (i.e., automatically).

Figure 5:
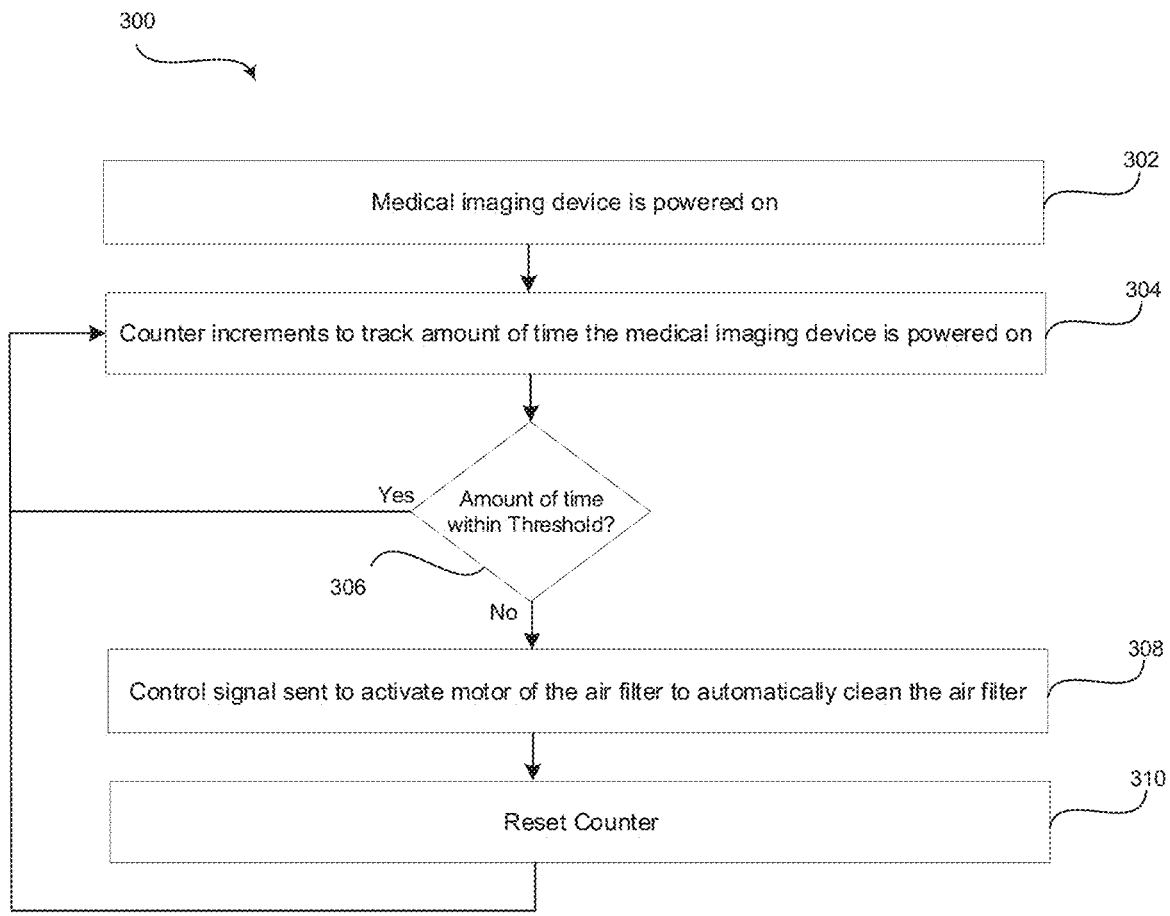
FIG. 5 is a flow chart illustrating exemplary steps that may be utilized for automatically cleaning air filters of a medical imaging system based on an amount of time the medical image device is powered on, in accordance with various embodiments.

FIG. 5 is a flow chart 300 illustrating exemplary steps 302-310 that may be utilized for automatically cleaning air filters 140, 160 of a medical imaging system 100 based on an amount of time the medical image device 100 is powered on, in accordance with various embodiments. Referring to FIG. 5, there is shown a flow chart 300 comprising exemplary steps 302 through 310. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 302, a medical imaging system 100 is powered on. For example, a user may flip a switch, push a button, plug in a power cord, and/or the like to turn on the medical imaging system 100. The powering on of the medical imaging system 100 causes an AC power box 130 to receive alternating current (AC) power that is converted by an AC/DC converter to direct current (DC) used to power the medical imaging system 100 components.

At step 304, a counter 118 increments to track an amount of time the medical imaging system 100 is powered on. For example, the counter 118 may comprise suitable logic, circuitry, interfaces and/or code that may be operable to track an amount of time the medical imaging system 100 is powered on. The counter 118 may be configured to continuously increment when the medical imaging system 100 is powered on until the medical imaging system 100 is powered off.

At step 306, an air filter processor 114 of the medical imaging system 100 may determine whether an amount of time that the medical imaging system 100 has been powered on is within a pre-determined threshold. For example, the air filter processor 114 may be configured to continuously or periodically monitor the counter 118 to determine when a current powered on time of the medical imaging system 100 exceeds a pre-determined threshold. The pre-determined threshold may be set by a manufacturer, vendor, user, or the like. For example, the pre-determined threshold may be 7 days, 30 days, 60 days, or any suitable amount of time. If the air filter processor 114 determines that the pre-determined threshold has not been exceeded, the process may return to step 304. If the air filter processor 114 determines that the pre-determined threshold has been exceeded, the process continues to step 308.

At step 308, the air filter processor 114 of the medical imaging system 100 may send a control signal to activate a motor of an air filter 140, 160 to automatically clean the air filter 140, 160. For example, the air filter processor 114 may be configured to send the control signal to one or more air filters 140, 160 of the medical imaging system 100. The motor 142, 162 of the air filter 140, 160 is activated in response to receiving the control signal from the air filter processor 114. The motor 142, 162 may be configured to rotate a drive shaft 144, 164 having grips 145 that engage slots 149 in a continuous belt air filter 148, 168 to translate the continuous belt air filter 148, 168 around the drive shaft 144, 164 and a rotatable passive shaft 146, 166. The translation of the filter 148, 168 causes the filter 148, 168 to move across a stationary filter brush 150, 170 pressed against outer sides of the filter 148, 168 and/or extending into the slots 149 of the filter 148, 168, which causes the filter brush 150, 170 to dislodge dust and other particles clinging to the filter 148, 168, thereby cleaning the filter 148, 168 without user intervention (i.e., automatically).

At step 310, the air filter processor 114 of the medical imaging system 100 may reset the counter 118. For example, the counter 118 may be reset and the process returns to step 304 where the counter 118 begins incrementing to track the amount of time the medical imaging system 100 has been powered on since the reset occurred.

Figure 6:
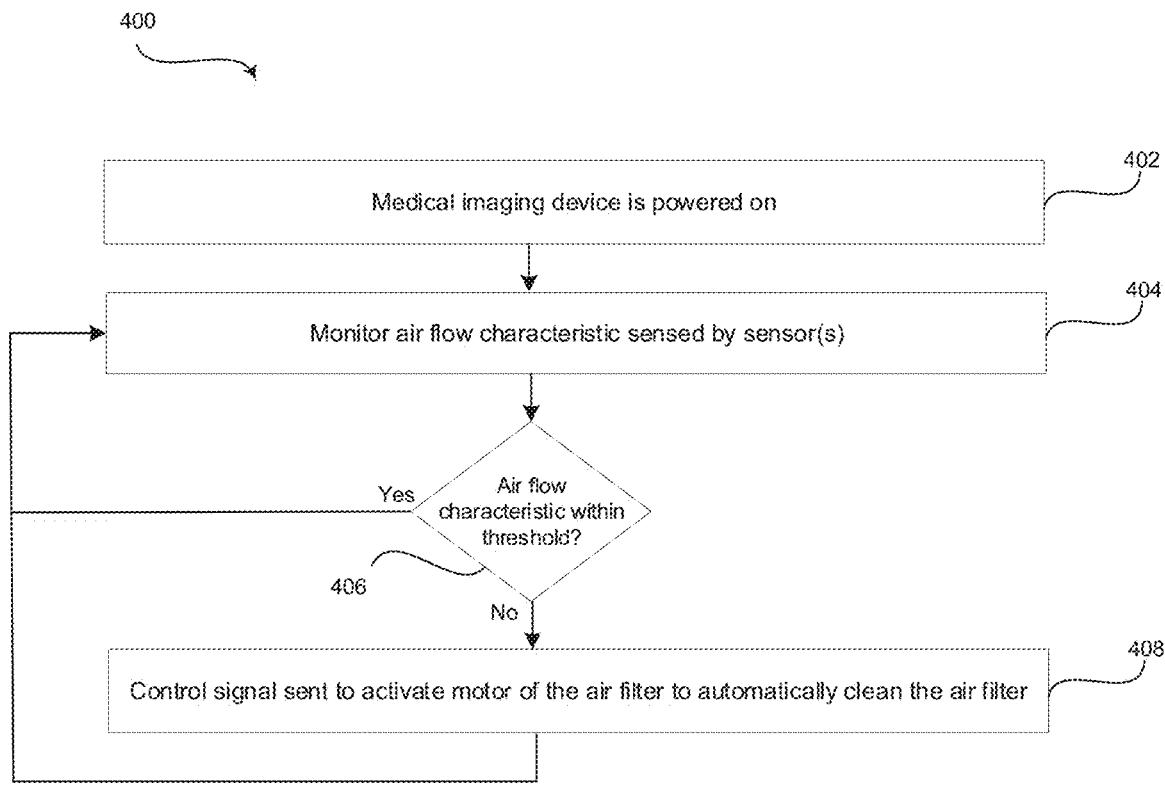
FIG. 6 is a flow chart illustrating exemplary steps that may be utilized for automatically cleaning air filters of a medical imaging system based on a detected air flow characteristic, in accordance with various embodiments.

FIG. 6 is a flow chart 400 illustrating exemplary steps 402-408 that may be utilized for automatically cleaning air filters 140, 160 of a medical imaging system 100 based on a detected air flow characteristic, in accordance with various embodiments. Referring to FIG. 6, there is shown a flow chart 400 comprising exemplary steps 402 through 408. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, a medical imaging system 100 is powered on. For example, a user may flip a switch, push a button, plug in a power cord, and/or the like to turn on the medical imaging system 100. The powering on of the medical imaging system 100 causes an AC power box 130 to receive alternating current (AC) power that is converted by an AC/DC converter to direct current (DC) used to power the medical imaging system 100 components.

At step 404, an air filter processor 114 of the medical imaging system 100 may monitor air flow characteristics sensed by sensor(s) 152, 172. For example, sensors 152, 172 positioned at air filters 140, 160 may detect air flow characteristics and provide the air flow characteristics to the air filter processor 114. The air flow characteristics may include mass flow rate through the air filter 140, 160, a pressure drop across the air filter 140, 160, or any suitable air flow characteristic. The sensor 152, 172 may be a mass flow rate sensor, a differential pressure sensor, or any suitable sensor.

At step 406, the air filter processor 114 of the medical imaging system 100 may determine whether the air flow characteristic is within a pre-determined threshold. For example, the air filter processor 114 may continuously or periodically monitor the air flow characteristics provided by sensors 152, 172 to determine when the air flow characteristic of one of more of the air filters 140, 160 of the medical imaging system 100 is outside of a pre-determined threshold. The pre-determined threshold may be set by a manufacturer, vendor, user, or the like. For example, the pre-determined threshold may be a minimum mass flow rate, a maximum pressure drop, or any suitable value of an air flow characteristic. If the air filter processor 114 determines that the air flow characteristic of a particular air filter 140, 160 does not fall outside of the pre-determined threshold associated with the particular air filter 140, 160, the process returns to step 404. If the air filter processor 114 determines that the air flow characteristic of a particular air filter 140, 160 fall outside of the pre-determined threshold associated with the particular air filter 140, 160, the process continues to step 408.

At step 408, the air filter processor 114 of the medical imaging system 100 may send a control signal to activate a motor of an air filter 140, 160 to automatically clean the air filter 140, 160. For example, the air filter processor 114 may be configured to send the control signal to one or more air filters 140, 160 of the medical imaging system 100. The motor 142, 162 of the air filter 140, 160 is activated in response to receiving the control signal from the air filter processor 114. The motor 142, 162 may be configured to rotate a drive shaft 144, 164 having grips 145 that engage slots 149 in a continuous belt air filter 148, 168 to translate the continuous belt air filter 148, 168 around the drive shaft 144, 164 and a rotatable passive shaft 146, 166. The translation of the filter 148, 168 causes the filter 148, 168 to move across a stationary filter brush 150, 170 pressed against outer sides of the filter 148, 168 and/or extending into the slots 149 of the filter 148, 168, which causes the filter brush 150, 170 to dislodge dust and other particles clinging to the filter 148, 168, thereby cleaning the filter 148, 168 without user intervention (i.e., automatically).

Aspects of the present disclosure provide a method 300, 400 and system 100 for automatically cleaning air filters 140, 160 of a medical imaging system 100. In accordance with various embodiments, the method 300, 400 may comprise monitoring 304, 404, by at least one processor 114 disposed in a housing 102 of a medical imaging system 100, an air filter operating condition. The method 300, 400 may comprise determining 306, 406, by the at least one processor 114, that the air filter operating condition is not within a pre-determined threshold. The method 300, 400 may comprise providing 308, by the at least one processor 114, a control signal to at least one air filter 140, 160. The at least one air filter 140, 160 comprises a motor 142, 162 configured to activate in response to the control signal. The at least one air filter 140, 160 comprises a drive shaft 144, 164 rotatably coupled to the motor 142, 162. The at least one air filter 140, 160 comprises a rotatable passive shaft 146, 166. The at least one air filter 140, 160 comprises a continuous belt air filter 148, 168 coupled to the drive shaft 144, 164 and the passive shaft 146, 166. The at least one air filter 140, 160 comprises a stationary filter brush 150, 170 mounted against the continuous belt air filter 148, 168. The method 300, 400 may comprise rotating 308, 408, by the motor 142, 162 in response to the control signal, the drive shaft 144, 164 to translate the continuous belt air filter 148, 168 around and between the drive shaft 144, 164 and the rotatable passive shaft 146, 166, and across the stationary filter brush 150, 170.

In an exemplary embodiment, the method 300, 400 may comprise drawing air 202, 206, by at least one fan 120, 134, into the housing 102 via the at least one air inlet 202, 206. The method 300, 400 may comprise passing the air 202, 206, by the at least one fan 120, 134, through the at least one air filter 140, 160. The method 300, 400 may comprise passing the air 202, 206, by the at least one fan 120, 134, across electronics 110, 130 disposed within the housing 102. The method 300, 400 may comprise expelling the air 204, 208, by the at least one fan 120, 134, from the at least one air outlet 106. In a representative embodiment, the electronics 110, 130 comprise at least one of an alternating current (AC) power box 130, or medical imaging electronics 112. In various embodiments, the method 300, 400 may comprise tracking 304, by a counter 118, an amount of time the medical imaging device 100 is powered on. The air filter operating condition may be the amount of time the medical imaging device 100 is powered on. The pre-determined threshold may be a maximum amount of time the medical imaging device 100 is powered on. In certain embodiments, the method 300, 400 may comprise detecting 404, by at least one sensor 152, 172, the air filter operating condition. The air filter operating condition may be at least one of a mass flow rate of air 202, 206 passing through the at least one air filter 140, 160, or an air pressure drop between an air inlet side of the at least one air filter 140, 160 and an air outlet side of the at least one air filter 140, 160. The threshold may be at least one of a minimum mass flow rate, or a maximum air pressure drop. In an exemplary embodiment, the at least one sensor 152, 172 is one or both of a mass flow rate sensor 152, 172, or a differential pressure sensor 152, 172. In a representative embodiment, the medical imaging system 100 may be an ultrasound system 100.

Various embodiments provide system for automatically cleaning air filters 140, 160 of a medical imaging system 100. The medical imaging system 100 may comprise a housing 102, at least one air filter 140, 160, and at least one processor 114. The housing 102 may comprise at least one air inlet 104, 108 and at least one air outlet 106. The at least one air filter comprise a motor 142, 162, a drive shaft 144, 164, a rotatable passive shaft 146, 166, a continuous belt air filter 148, 168, and a stationary filter brush 150, 170. The drive shaft 144, 164 may be rotatably coupled to the motor 142, 162. The continuous belt air filter 148, 168 may be coupled to the drive shaft 144, 164 and the passive shaft 146, 166. The stationary filter brush 150, 170 may be mounted against the continuous belt filter 148, 168. The activation of the motor 142, 162 may rotate the drive shaft 144, 164 to translate the continuous belt air filter 148, 168 around and between the drive shaft 144, 164 and the rotatable passive shaft 146, 166, and across the stationary filter brush 150, 170. The at least one processor 114 may be disposed within the housing 102. The at least one processor 114 may be configured to monitor an air filter operating condition. The at least one processor 114 may be configured to determine that the air filter operating condition is not within a pre-determined threshold. The at least one processor 114 may be configured to provide a control signal to activate the motor 142, 162 in response to the air filter operating condition being not within the pre-determined threshold.

In a representative embodiment, the medical imaging system 100 may comprise at least one fan 120, 134. The at least one fan 120, 134 may be operable to draw air 202, 206 into the housing 102 via the at least one air inlet 104, 108. The at least one fan 120, 134 may be operable to pass the air 202, 206 through the at least one air filter 140, 160. The at least one fan 120, 134 may be operable to pass the air 202, 206 across electronics 110, 130 disposed within the housing 102. The at least one fan 120, 134 may be operable to expel the air 204, 208 from the at least one air outlet 106. In various embodiments, the electronics 110, 130 comprise at least one of an alternating current (AC) power box 130, or medical imaging electronics 112. In certain embodiments, the air filter operating condition may be an amount of time the medical imaging device 100 is powered on. The pre-determined threshold may be a maximum amount of time the medical imaging device 100 is powered on. In an exemplary embodiment, the medical imaging system 100 may comprise a counter 118 configured to track the amount of time the medical imaging device 100 is powered on. In a representative embodiment, the air filter operating condition may be at least one of a mass flow rate of air 202, 206 passing through the at least one air filter 140, 160, or an air pressure drop between an air inlet side of the at least one air filter 140, 160 and an air outlet side of the at least one air filter 140, 160. The threshold may be at least one of a minimum mass flow rate, or a maximum air pressure drop. In various embodiments, the medical imaging system 100 may comprise at least one sensor 152, 172 configured to detect the air filter operating condition. In certain embodiment, the at least one sensor 152, 172 is one or both of a mass flow rate sensor 152, 172, or a differential pressure sensor 152, 172. In an exemplary embodiment, the medical imaging system 100 may be an ultrasound system 100.

Certain embodiments provide a non-transitory computer readable medium having stored thereon, a computer program having at least one code section. The at least one code section is executable by a machine for causing a medical imaging system 100 to perform steps 300, 400. The steps 300, 400 may comprise monitoring 304, 404 an air filter operating condition. The steps 300, 400 may comprise determining 306, 406 that the air filter operating condition is not within a pre-determined threshold. The steps 300, 400 may comprise providing 308, 408 a control signal to at least one air filter 140, 160. The at least one air filter 140, 160 may comprise a motor 142, 162 configured to activate in response to the control signal. The at least one air filter 140, 160 may comprise a drive shaft 144, 164 rotatably coupled to the motor 142, 162. The at least one air filter 140, 160 may comprise a rotatable passive shaft 146, 166. The at least one air filter 140, 160 may comprise a continuous belt air filter 148, 168 coupled to the drive shaft 144, 164 and the passive shaft 146, 166. The at least one air filter 140, 160 may comprise a stationary filter brush 150, 170 mounted against the continuous belt air filter 148, 168. The motor 142, 162, in response to the control signal, may rotate the drive shaft 144, 164 to translate the continuous belt air filter 148, 168 around and between the drive shaft 144, 164 and the rotatable passive shaft 146, 166, and across the stationary filter brush 150, 170.

In various embodiments, the steps 300, 400 may comprise tracking 304 an amount of time the medical imaging device 100 is powered on. The air filter operating condition may be the amount of time the medical imaging device 100 is powered on. The pre-determined threshold may be a maximum amount of time the medical imaging device 100 is powered on. In certain embodiments, the steps 300, 400 may comprise receiving 404 the air filter operating condition detected by at least one sensor 152, 172. The air filter operating condition may be at least one of a mass flow rate of air 202, 206 passing through the at least one air filter 140,

160, or an air pressure drop between an air inlet side of the at least one air filter 140, 160 and an air outlet side of the at least one air filter 140, 160. The threshold may be at least one of a minimum mass flow rate, or a maximum air pressure drop. In an exemplary embodiment, the medical imaging system 100 may be an ultrasound system 100.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for automatically cleaning air filters of a medical imaging system.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
   monitoring, by at least one processor disposed in a housing of a medical imaging system, an air filter operating condition, wherein the housing comprises at least one air inlet and at least one air outlet;
   determining, by the at least one processor, that the air filter operating condition is not within a pre-determined threshold;
   providing, by the at least one processor, a control signal to at least one air filter, wherein the at least one air filter comprises:
   a motor configured to activate in response to the control signal;
   a drive shaft rotatably coupled to the motor;
   a rotatable passive shaft;
   a continuous belt air filter coupled to the drive shaft and the passive shaft; and
   a stationary filter brush mounted against the continuous belt air filter; and
   rotating, by the motor in response to the control signal, the drive shaft to translate the continuous belt air filter around and between the drive shaft and the rotatable passive shaft, and across the stationary filter brush.

2. The method of claim 1, comprising:
   drawing air, by at least one fan, into the housing via the at least one air inlet,
   passing the air, by the at least one fan, through the at least one air filter,
   passing the air, by the at least one fan, across electronics disposed within the housing, and
   expelling the air, by the at least one fan, from the at least one air outlet.

3. The method of claim 2, wherein the electronics comprise at least one of:
   an alternating current (AC) power box, or
   medical imaging electronics.

4. The method of claim 1, comprising tracking, by a counter, an amount of time the medical imaging system is powered on, wherein:
   the air filter operating condition is the amount of time the medical imaging system is powered on, and
   the pre-determined threshold is a maximum amount of time the medical imaging system is powered on.

5. The method of claim 1, comprising detecting, by at least one sensor, the air filter operating condition, wherein:
   the air filter operating condition is at least one of:
   a mass flow rate of air passing through the at least one air filter, or
   an air pressure drop between an air inlet side of the at least one air filter and an air outlet side of the at least one air filter, and
   the pre-determined threshold is at least one of:
   a minimum mass flow rate, or
   a maximum air pressure drop.

6. The method of claim 5, wherein the at least one sensor is one or both of:
   a mass flow rate sensor, or
   a differential pressure sensor.

7. The method of claim 1, wherein the medical imaging system is an ultrasound system.

8. The method of claim 1, wherein the stationary filter brush is mounted between the drive shaft and the rotatable passive shaft and held against both outer sides of the continuous belt air filter.

9. A medical imaging system comprising:
a housing having at least one air inlet and at least one air outlet;
at least one air filter comprising:
a motor;
a drive shaft rotatably coupled to the motor;
a rotatable passive shaft;
a continuous belt air filter coupled to the drive shaft and the passive shaft; and
a stationary filter brush mounted against the continuous belt filter,
wherein activation of the motor rotates the drive shaft to translate the continuous belt air filter around and between the drive shaft and the rotatable passive shaft, and across the stationary filter brush; and
at least one processor disposed within the housing, the at least one processor configured to:
monitor an air filter operating condition;
determine that the air filter operating condition is not within a pre-determined threshold; and
provide a control signal to activate the motor in response to the air filter operating condition being not within the pre-determined threshold.

10. The medical imaging system of claim 9, comprising at least one fan operable to:
draw air into the housing via the at least one air inlet,
pass the air through the at least one air filter,
pass the air across electronics disposed within the housing, and
expel the air from the at least one air outlet.

11. The medical imaging system of claim 10, wherein the electronics comprise at least one of:
an alternating current (AC) power box, or
medical imaging electronics.

12. The medical imaging system of claim 9, wherein:
the air filter operating condition is an amount of time the medical imaging system is powered on, and
the pre-determined threshold is a maximum amount of time the medical imaging system is powered on.

13. The medical imaging system of claim 12, comprising a counter configured to track the amount of time the medical imaging system is powered on.

14. The medical imaging system of claim 8, wherein:
the air filter operating condition is at least one of:
a mass flow rate of air passing through the at least one air filter, or
an air pressure drop between an air inlet side of the at least one air filter and an air outlet side of the at least one air filter, and
the pre-determined threshold is at least one of:
a minimum mass flow rate, or
a maximum air pressure drop.

15. The medical imaging system of claim 14, comprising at least one sensor configured to detect the air filter operating condition.

16. The medical imaging system of claim 15, wherein the at least one sensor is one or both of:
a mass flow rate sensor, or
a differential pressure sensor.

17. The medical imaging system of claim 9, wherein the medical imaging system is an ultrasound system.

18. The medical imaging system of claim 9, wherein the stationary filter brush is mounted between the drive shaft and the rotatable passive shaft and held against both outer sides of the continuous belt air filter.

19. A non-transitory computer readable medium having stored thereon, a computer program having at least one code section, the at least one code section being executable by a machine for causing a medical imaging system to perform steps comprising:
monitoring an air filter operating condition;
determining that the air filter operating condition is not within a pre-determined threshold; and
providing a control signal to at least one air filter, wherein the at least one air filter comprises:
a motor configured to activate in response to the control signal;
a drive shaft rotatably coupled to the motor;
a rotatable passive shaft;
a continuous belt air filter coupled to the drive shaft and the passive shaft; and
a stationary filter brush mounted against the continuous belt air filter; and
wherein the motor, in response to the control signal, rotates the drive shaft to translate the continuous belt air filter around and between the drive shaft and the rotatable passive shaft, and across the stationary filter brush.

20. The non-transitory computer readable medium of claim 19, wherein:
the steps further comprise tracking an amount of time the medical imaging system is powered on,
the air filter operating condition is the amount of time the medical imaging system is powered on, and
the pre-determined threshold is a maximum amount of time the medical imaging system is powered on.

21. The non-transitory computer readable medium of claim 19, wherein:
the steps further comprise receiving the air filter operating condition detected by at least one sensor,
the air filter operating condition is at least one of:
a mass flow rate of air passing through the at least one air filter, or
an air pressure drop between an air inlet side of the at least one air filter and an air outlet side of the at least one air filter, and
the pre-determined threshold is at least one of:
a minimum mass flow rate, or
a maximum air pressure drop.

22. The non-transitory computer readable medium of claim 19, wherein the medical imaging system is an ultrasound system.

23. The non-transitory computer readable medium of claim 19, wherein the stationary filter brush is mounted between the drive shaft and the rotatable passive shaft and held against both outer sides of the continuous belt air filter.

* * * * *